United States Patent
Olson

(12) 
(10) Patent No.: US 9,320,570 B2
(45) Date of Patent: Apr. 26, 2016

(54) SYSTEM AND METHOD FOR PREVENTING COLLATERAL DAMAGE WITH INTERVENTIONAL MEDICAL PROCEDURES

(75) Inventor: Eric S. Olson, Maplewood, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1919 days.

(21) Appl. No.: 12/335,980

(22) Filed: Dec. 16, 2008

(65) Prior Publication Data

US 2009/0171338 A1  Jul. 2, 2009

Related U.S. Application Data

(60) Provisional application No. 61/017,366, filed on Dec. 28, 2007.

(51) Int. Cl.
*A61B 19/00* (2006.01)
*A61B 17/00* (2006.01)

(52) U.S. Cl.
CPC ............ *A61B 19/5244* (2013.01); *A61B 19/40* (2013.01); *A61B 2017/00119* (2013.01); *A61B 2017/00243* (2013.01)

(58) Field of Classification Search
CPC ................. A61B 19/5244; A61B 2019/5287; A61B 2019/5272; A61B 2019/5268; A61B 2017/00119; A61B 2017/00123; A61B 2017/00128
See application file for complete search history.

(56) References Cited

U.S. PATENT DOCUMENTS

| | | | |
|---|---|---|---|
| 5,391,199 A | 2/1995 | Ben-Haim | |
| 5,697,377 A | 12/1997 | Wittkampf | |
| 5,938,603 A | 8/1999 | Ponzi | |
| 6,115,626 A * | 9/2000 | Whayne et al. | 600/427 |
| 6,129,669 A | 10/2000 | Panescu et al. | |
| 7,263,397 B2 * | 8/2007 | Hauck et al. | 600/374 |
| 7,678,070 B2 * | 3/2010 | Kumar et al. | 604/31 |
| 7,757,694 B2 * | 7/2010 | Ritter et al. | 128/898 |
| 7,894,871 B2 * | 2/2011 | Wittkampf et al. | 600/372 |
| 7,974,674 B2 * | 7/2011 | Hauck et al. | 600/374 |
| 8,454,538 B2 * | 6/2013 | Wittkampf et al. | 600/587 |
| 8,528,565 B2 * | 9/2013 | Hauck et al. | 128/898 |
| 8,660,635 B2 * | 2/2014 | Simon et al. | 600/424 |
| 2006/0094956 A1 * | 5/2006 | Viswanathan | 600/431 |
| 2007/0022558 A1 * | 2/2007 | Petkov et al. | 15/250.361 |
| 2008/0161668 A1 * | 7/2008 | Wittkampf et al. | 600/372 |
| 2008/0221425 A1 * | 9/2008 | Olson et al. | 600/407 |
| 2010/0168558 A1 * | 7/2010 | Olson | 600/424 |

* cited by examiner

*Primary Examiner* — Andrew Gilbert
(74) *Attorney, Agent, or Firm* — Dykema Gossett PLLC

(57) ABSTRACT

A system for performing an interventional medical procedure is disclosed. The system includes a treatment device having a treatment portion, a localization system, and a means for defining a boundary about the treatment portion relative to location data point. The system may further be configured to provide a response when a portion of the treatment device enter or leaves a defined boundary, region, or range. Methods for performing interventional medical procedures that, among other things, reduce or prevent collateral damage to non-target regions are also disclosed.

20 Claims, 5 Drawing Sheets

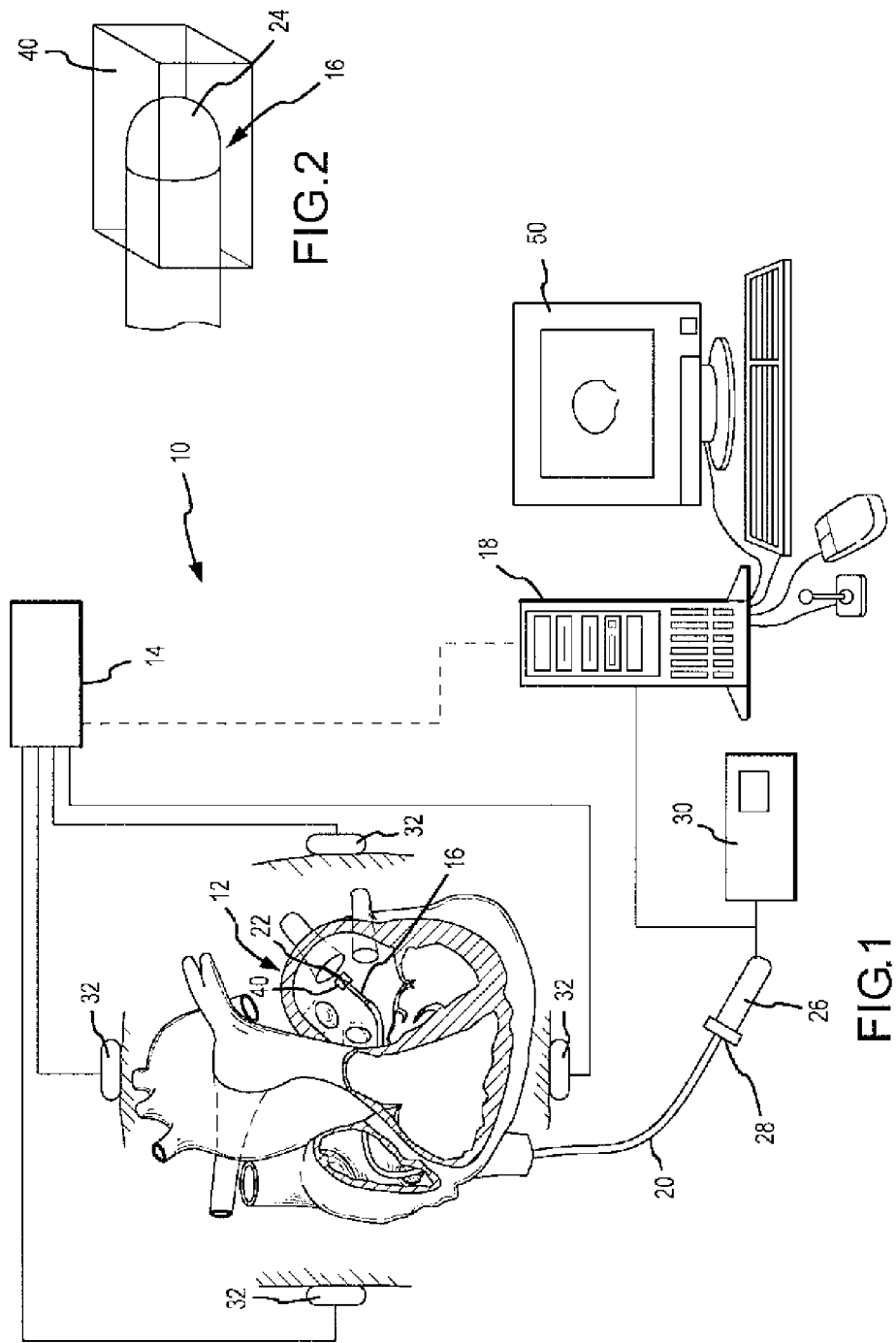

SYSTEM AND METHOD FOR PREVENTING COLLATERAL DAMAGE WITH INTERVENTIONAL MEDICAL PROCEDURES

CROSS-REFERENCE TO RELATED APPLICATION

This application claims the benefit of U.S. provisional application No. 61/017,366, filed Dec. 28, 2007, which is hereby incorporated by reference as though fully set forth herein.

BACKGROUND OF THE INVENTION a. Field of the Invention

The instant invention relates to medical intervention systems and methods. The instant invention includes a method and system for performing an interventional medical procedure, such as ablation procedures that reduce or prevent collateral damage during catheter ablation utilizing motion-related detection.

b. Background Art

The visualization and treatment of organs and tissues has been advanced through the increasing use of medical devices, including catheter systems. Catheter systems have been designed for the incorporation of various components to treat and diagnose ailments, as accomplished through the mapping of organs, sensing of thermal and electrical changes exhibited by a tissue (e.g., heart), as well as the application of energizing sources (such as radiofrequency, cryogenics, laser, and high frequency ultrasound) to tissue.

It is known to generate anatomical geometries in connection with various diagnostic or therapeutic procedures. For example, it is known to use multiple measurements, which may for instance be taken as a catheter is moved within a heart chamber, to generate a cloud of geometry points (or "location data points") that may be used to provide a physical geometry, such as a heart chamber. Various surface construction programs may be employed to provide a representation of a chamber or other anatomical element.

During treatments, such as ablation therapy, an operator routinely desires to maintain a medical device, such as a catheter tip, at a stable location, or to move the device in a controlled manner to perform a procedure. However, the positioning of the device, and maintaining position or coordinated movement of the device, can be complicated by dynamics associated with the treatment environment. For example, in connection with cardiac procedures, the beating of the heart can make associated treatments more challenging. Moreover, in many treatment environments where treatment targets exist, there are commonly collateral or surrounding areas where treatment, such as ablation, are not desired.

BRIEF SUMMARY OF THE INVENTION

A system for performing an interventional medical procedure is disclosed. The system includes a treatment device having a treatment portion, a localization system, and a means for defining a boundary about the treatment portion relative to location data point. The system may further be configured to provide a response when a portion of the treatment device enter or leaves a defined boundary or path. The system may also include one or more additional "reference" devices, e.g., catheters or probes, that may be placed at or about sensitive areas in a treatment environment such that the system can provide a desired response if the treatment device and/or treatment portion comes within a select range of the reference device or portion thereof. Methods for performing interventional medical procedures that, among other things, reduce or prevent collateral damage to non-target regions are also disclosed.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1 is schematic illustration of a system for performing an interventional medical procedure in accordance with an embodiment of the invention;

FIG. 2 is a partial perspective view of a catheter tip in accordance with an embodiment of the invention;

DETAILED DESCRIPTION OF THE INVENTION

Figure 3:
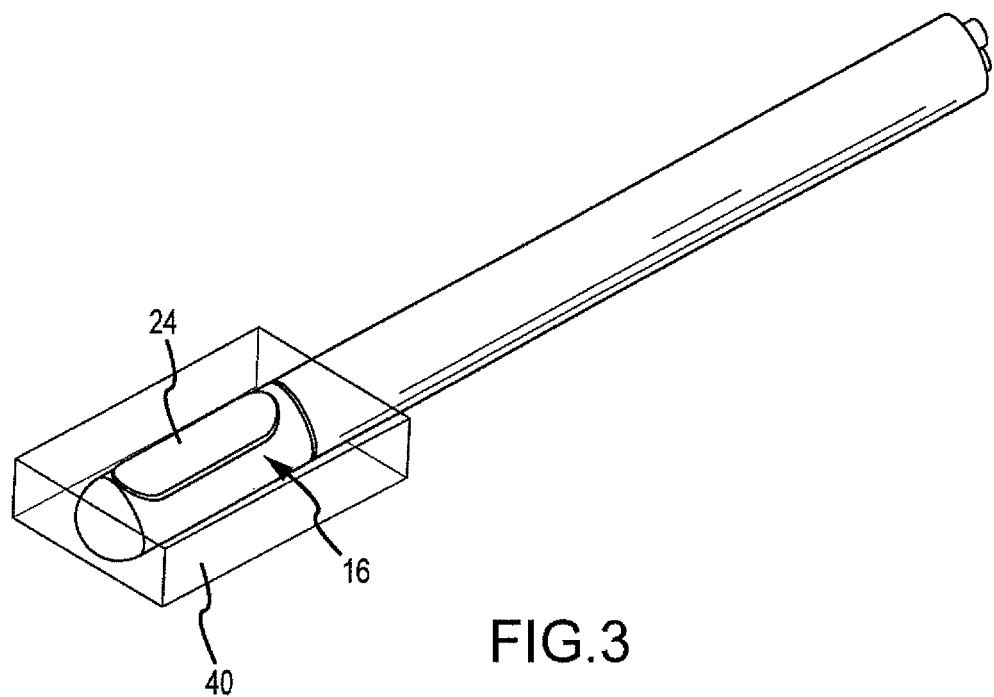
FIG. 3 is a partial perspective view of another catheter tip in accordance with an embodiment of the invention.

Referring now to the drawings wherein like reference numerals are used to identify like components in the various views, and in particular to FIG. 1, a schematic illustration of a system 10 for performing an interventional medical procedure in accordance with an embodiment of the invention. System 10 is shown treating a physiological element, such as tissue or an organ (e.g., heart 12). The illustrated system 10 includes a localization system 14, a treatment device 16; and at least one processor 18.

The treatment device 16 may be configured for insertion into a patient, for example, into a patient's heart. The treatment device may comprise a catheter, such as an intra-cardiac catheter 20 (or probe) of the type generally depicted. However, the invention is not limited to the device as shown, and other devices for various interventional medical procedures are contemplated. As illustrated, treatment device 16 may comprise a distal end 22 with a treatment portion 24. The treatment portion may direct energy (e.g., radio frequency (RF), ultrasound, high frequency ultrasound (HIFU), microwave, laser, etc.) to a target or treatment side and may comprise, for example, an electrode tip or other portion providing a means for providing energy to perform ablation. Moreover, the treatment device may be connected to or formed with catheter 20.

Catheter 20 may further include a handle 26 and a proximal end 28 that a doctor may operate. For some embodiments, a longitudinal drive or servo mechanism 30 may be connected to and associated with the movement of the catheter 20 and/or the device 16. If desired, the positioning of the catheter 20 and/or the associated treatment device 16 may be, at least in part, robotically operated or controlled, for instance, by a servo mechanism.

Figure 4:
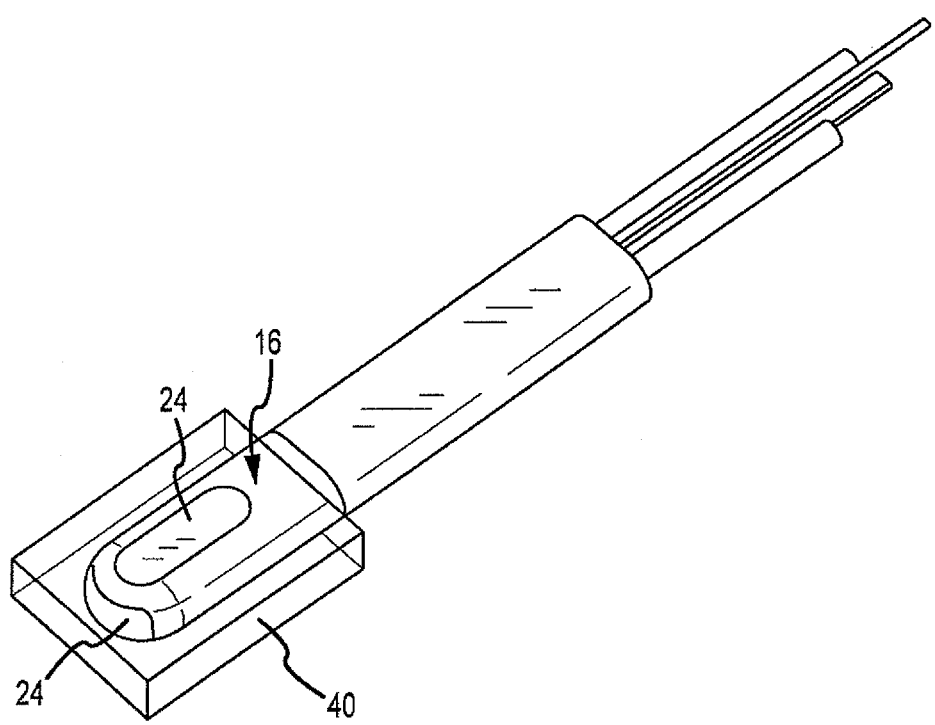
FIG. 4 is a partial perspective view of yet another catheter tip in accordance with an embodiment of the invention.
Figure 5:
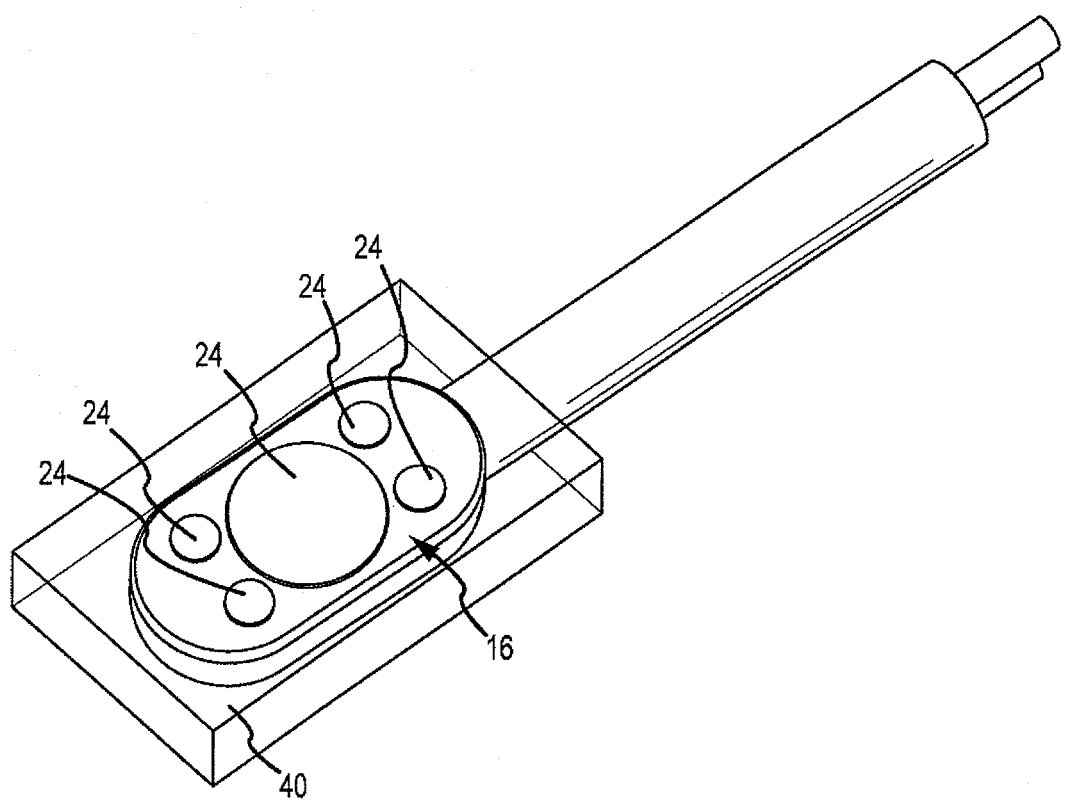
FIG. 5 is a partial perspective view of still another catheter tip in accordance with an embodiment of the invention.

The treatment device, including the treatment portion associated therewith, need not be identical to that illustrated in FIGS. 1 and 2. Other examples of distal portions of treatment devices 16, and associated treatment portions 24, are generally illustrated in FIGS. 3, 4, and 5. However, it is important to note that the invention is not limited to the specific exemplary configurations shown, and a wide variety of other treatment device configurations are contemplated by and within the scope and spirit of the invention.

The localization system 14 (sometimes also referred to as a "mapping system," "navigation system," or "positional feedback system") may be used to measure location data (e.g., data points) indicative of the location of the treatment device 16, or a point or portion thereof. The localization system may, for example as illustrated, include a plurality of paired electrodes 32 that define measurement axes for locating treatment device 16 within a physical environment using electrical potentials. By way of example, without limitation, the localization system 14 may comprise the EnSite NavX™ navigation and visualization system of St. Jude Medical, Inc. or the CARTO navigation system marketed by Biosense Webster, Inc., although various other systems known in the art for monitoring the position of a point or area associated with an interventional treatment device may be utilized without departing from the spirit and scope of the invention. In an embodiment, the localization system 14 may provide location data points for treatment device 16 (or a point or portion thereof) within a treatment environment (e.g., heart 12) in space, for instance, relative to a three-dimensional Cartesian coordinate system including an x-axis, a y-axis, and a z-axis. It is understood by those in the field that alternative systems for measuring and/or expressing position information relative to the treatment device (or portions thereof), such as spherical coordinates, or other systems providing GPS-like abilities (for a medical device environment) are contemplated by the invention. Consequently, the position in space of the treatment device 16, or portions thereof (such as the portion performing ablation) can be determined and expressed in mathematical or data form.

The localization system 14 and treatment device 16 may be coupled or otherwise in operational communication (e.g., via wireless signal) with at least one processor 18. Processor 18 may be incorporated with (or may be physically separate from) the localization system 14 and may, among other things, record one or more measured positional data points corresponding to the physical structure of the relevant treatment device, the environment being treated, or the position and movement of the treatment device, in memory. Processor 18 may additionally define a geometric boundary (e.g., a boundary that includes a defined square, rectangular, sphere, ellipse, or other geometry or geometries) about or relative to a current position of at least a portion of the treatment device 16 or treatment portion 24. The geometric boundary (e.g., generally depicted as 40 in FIG. 1) may be relative to a specific or select location data point and may provide an operational region (a defined region or range in which the treatment device may be activated or operational) within the boundary. The size or configuration of the geometric boundary (relative to the location data point) may be programmed or selected by a user. For example, without limitation, the geometric boundary could be a radius (e.g., a 5 mm radius) about an established location data point. Where the environment involves dynamic action, such as a beating heart, the system can provide an appropriate boundary or operational region relative to the environment (e.g., the boundary may be expanded to allow for a range of motion proportionate to that expected in connection with a moving or dynamic environment). Further, for some applications, the geometric boundary or operational region therein may change or be redefined over time—for example, in response to effectuated treatment.

The localization system 14 and/or processor 18 may further be configured to provide a response in the event the treatment portion 24 of the treatment device 16 is determined to be (or have moved) outside of the operational region (e.g., to have violated a system parameter). The response may comprise one or more of several different types of responses, and may comprise an audible signal, a visual signal, or audible and visual signals, and various multiples and combinations thereof, which may further differ by time and relative positioning (e.g., the positioning (or changing position) of the treatment device or treatment portion relative to a boundary). By way of example, without limitation, the system may provide an initial response (e.g., a "warning track" response) when the treatment portion of the device deviates by a given degree from a set location data point, and then may provide a heightened or full response if the device reaches a second, further degree of deviation from the location data point. If desired, the system 14 and/or processor 18 may further be, directly or indirectly, connected to a computer 50, a screen, or various other forms of graphical user interfaces, or combinations thereof, as are known in the field.

For some applications and embodiments, when the treatment device (or treatment portion thereof) moves to or beyond the geometric boundary or outside of the operational region, the treatment portion may automatically be rendered inoperable by the system. Further, for some embodiments, the system 10 may be configured to permit the treatment portion 24 to again become operable once all or a portion of the treatment device 16 or treatment portion 24 returns (at least to a defined extent) within the then-in-effect operational region. For some applications, the system must additionally be specifically authorized for "re-set" in some form by the operator.

It is noted that for some applications, the operational region created by, for example, processor 18 may be, at least in part, related to the movement, i.e., velocity or acceleration, associated with the treatment device as it moves (e.g., along a treatment path). That is, the system may collect and filter data points associated with a treatment device based upon its movement rather than, or in addition to, its position. An example of a system that periodically measures the location of a treatment device, determines its velocity, and detects and utilizes relevant changes, at least in part, associated with the velocity is disclosed in U.S. patent application Ser. No. 11/647,591, filed on Dec. 29, 2006, which issued as U.S. Pat. No. 7,894,871 on Feb. 22, 2011, and titled "Filtering Method for Surface Modeling," which is hereby incorporated by reference in its entirety as though fully set forth herein. For instance, for some applications, therapies could be automatically terminated if the motion of the treatment device becomes ballistic. Moreover, in an embodiment of the invention, if an associated geometric boundary and/or operational region is chosen or provided (e.g., by drawing a path (including a treatment path or a portion of a treatment path) on a surface of a model, such as a virtual model, and defining an operational region along that path), it may be desirable to limit the speed at which the medical device progresses along the established treatment path. Undesirably rapid or slow movement of the device (i.e., movement that is outside of a defined range of acceptable velocity and/or acceleration), even within an associated geometric boundary and/or operational region, may be indicative of an motion that is not deliberate or intended, and may consequently produce a desired response (e.g., indicating a violated system parameter), which may include the immediate termination of an associated treatment or therapy.

FIGS. 3, 4 and 5 generally illustrate a several variations of potential treatment devices 16 contemplated by the invention. The illustrated treatment devices, which may comprise ablation catheters for ablation, are shown including various treatment portions 24. The treatment portions may include transducers or other means for imparting energy to a target.

Additionally, for illustrative purposes, a somewhat generic geometric boundary and/or operational range 40 associated with each device 16 is also illustrated. Of course, the geometric boundaries and/or operational ranges 40 illustrated in FIGS. 3-5 are not limited to those depicted. That is, such boundaries and/or ranges 40 may be take other forms and can readily be modified or changed, for example by a processor associated with the system, to provide various other geometric configurations and to adapt to various dynamic conditions and intended treatment environments.

Figure 6:
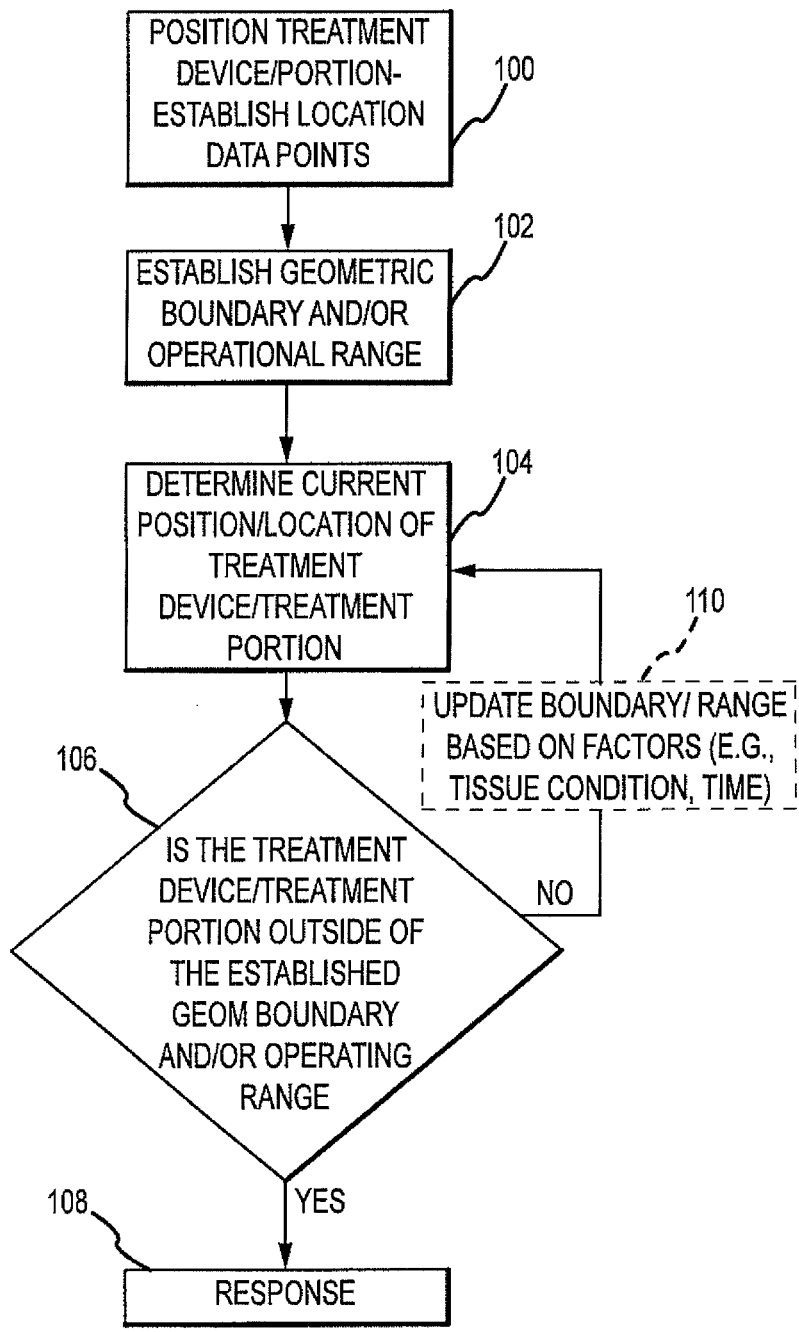
FIG. 6 is a flowchart of an exemplary method according to an embodiment of the present invention.

The flowchart of FIG. 6 generally outlines an exemplary system and methodology in accordance with a first embodiment of the invention. For instance, in some applications, a surgeon wants to perform ablation at a select location and wants the treatment portion 24 of a treatment device 16 to remain—at least for some period of time—at or within an acceptable range of a select location data point (which in some contexts may also be referred to as an "anchor point"). As generally presented at step 100, a treatment portion 24 of a treatment device 26 is positioned for operational contact with a treatment target and, via a localization system, a location data point (i.e., anchor point) is established. At step 102, a corresponding geometric boundary and/or operational range is established and set relative to the established location data point. The operational range can be established in a number of ways. For instance, by way of a first example, a system control may instruct the system to sample the treatment device's current location and establish a boundary about one or more detected points. In a second example, the system may automatically detect the application of a therapy by a device and set up a related boundary. For instance, automatic detection of RF energy can be accomplished by monitoring electrical signals associated with the treatment device. By way of example, without limitation, such an implementation is generally provided in connection with the EnSite NavX™ navigation and visualization system of St. Jude Medical, Inc. In a third example, a separate therapy system can send a signal to an interventional navigation system that indicates that the treatment device has initiated therapy. For example, this could be accomplished with generators via ports that already may report energy, temperature, impedance, etc. Moreover, even in cases where a boundary is initially established automatically, for some embodiments a user may be permitted to reset the operational region to a boundary that is, for example, based on an updated or current position of the treatment device or a portion thereof. Such a later-established or "reset" boundary can provide for gradual, deliberate movement of the medical device, and allow for a reset if the medical device, for instance, enters a "warning zone" and the user wants to silence or end the warning and adapt to or for the new location.

At step 104, the localization system determines the current position/location of the treatment device and/or treatment portion. At step 106, the system (e.g., via processor) determines if the treatment device and/or treatment portion is within the established geometric boundary and/or operational range. If the system determines that the treatment device and/or treatment portion is not within the established geometric boundary and/or operational range, some form of response (step 108), including those previously noted, is provided. If the system determines that the treatment device and/or treatment portion is within (or not outside of) the established geometric boundary and/or operational range, continued operation of the system is permitted, no response is provided, and (within a short period of time, which may be virtually imperceptible to the user) the system will return to and repeat step 104. As indicate in the exemplary flowchart, before returning to step 104, the system may optionally (step 110) perform, e.g., under some pre-defined conditions, "update" or revise the geometric boundary and/or operational range based upon certain factors. For instance, the system may update/revise the geometric boundary and/or operational range based on an assessment of the treatment (e.g., a factor associated with the treatment site, such as heat, perhaps provided by a sensor) and/or passage of a period(s) of time. In another embodiment, the boundary range may be updated to allow for a slow migration of the treatment device, for instance, when the treatment objective is to provide a gradual, but not ballistic, type of movement.

In connection with another embodiment of the invention, a user may provide the system with a path for treatment, e.g., a path for ablation. If desired, the prescribed treatment path may be provided in connection with collected data provided by a localization, navigation, or mapping system. The user can then provide (e.g., use a mouse to draw) an intended path on a model (e.g., mathematical surface model) of the target and related environment. The system can then set up a geometric boundary (which could take the form of a tube around the intended path), which may change with respect to time. That is, at a given time in the procedure, movement of the treatment device may be anticipated or expected, and the boundary and/or operational range along the path may be able to be updated automatically using various applicable or desired algorithms.

In yet another embodiment of the invention, there may be a defined area (e.g., the atrial ventricular node) that the system is designed to avoid. For such an embodiment, the system may provide a model for the environment, define a geometric boundary or non-operational region about the physical area to be avoided. Then, if the treatment device reaches or comes within a select range of the geometric boundary or non-operational region, a response (which may, for example, include the rendering of the device inoperable) can be provided.

In another embodiment of the invention, a surface model of the treatment environment (e.g., a surface model for a chamber of a heart) is provided. The system may be configured to provide a response if the treatment device and/or treatment portion leaves the surface (by some defined amount). The system may, in addition or in lieu of the foregoing, also provide certain regions or planes (in two or three-dimensional space) that the treatment device and/or treatment portion may not cross without response. For instance, in a cardiac environment, a prohibited region or prohibited plane may be established at, or in advance of, an entrance to certain valves. Such a configuration may be advantageous, for example, to prevent application of energy to a separate chamber of a heart or a wholly different region of a body.

In yet another embodiment, in lieu of, or in addition to, working with a "mapped" treatment environment, the system may employ one or more additional medical devices (i.e., "reporting device"), such as catheters or probes, that can be positioned at sensitive areas in the treatment environment. Such sensitive areas may include portions or regions where treatment (e.g., the undesired application of energy) is not desired or could be problematic. For example, in the cardiac environment, a reporting device may be positioned at or about an area with sensitive electrical cardiac activity (e.g., the AV node or the HIS bundle) or at other sensitive positions that may move with the beating of the heart. The system may then be configured so a response, which as described above may include various responses, including the automatic de-activation of the treatment device and/or treatment portion, if the treatment device and/or treatment portion is determined to have come within a predetermined or select range of the reporting device.

Additionally, the system can be adapted to take into account the interruption of treatment source. Such an adaptation may be accomplished in several ways. For example, in a first embodiment, if ablation energy is passed through a localization device (e.g., as done with the EnSite NavX system) the energy could be terminated by breaking the connection to the treatment device (e.g., catheter). The breaking of the connection could be facilitated via a relay mechanism controlled by the localization system. In another embodiment, a communication signal could be sent to the device that is providing the treatment or therapy energy (e.g., RF energy). The communication signal, which may be a command, could be sent to the device providing the energy, and that device could be responsible for termination of the treatment or therapy.

Although a number of embodiments of this invention have been described above with a certain degree of particularity, those skilled in the art could make numerous alterations to the disclosed embodiments without departing from the spirit or scope of this invention. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A system for performing an interventional medical procedure using a treatment device comprising a distal end having a treatment portion, the system comprising:
   a localization system for providing a location data point indicative of a location of the treatment portion; and
   a processor (i) configured to define and maintain during the procedure a boundary about the treatment portion based on and relative to the location data point as a respective location of the location data point changes during the procedure and (ii) configured to provide and maintain during the procedure an operational region within the boundary;
   wherein the processor is further configured to provide a response whenever the location data point indicates that the treatment portion is located outside of the operational region.

2. The system of claim 1, wherein the boundary includes a geometric boundary defined relative to at least a portion of the treatment portion, and wherein the geometric boundary includes a portion that is square, rectangular, spherical, or elliptical.

3. The system of claim 1, wherein the operational region changes over time.

4. The system of claim 1, wherein the treatment portion is configured to direct energy to a target.

5. The system of claim 1, wherein the response comprises an audible signal, a visual signal, or an audible and visual signal.

6. The system of claim 1, wherein the processor is configured to provide an initial response and one or more additional responses at given relative positions of the location data point and the operational region.

7. The system of claim 1, wherein the treatment device includes a catheter.

8. The system of claim 1, wherein the processor is further configured to inhibit delivery of treatment energy to the treatment portion whenever the location data point indicates that the treatment portion is located outside of the boundary.

9. The system of claim 8, wherein the processor is further configured to enable delivery of treatment energy to the treatment portion whenever at least a portion of the treatment portion returns within the operational region.

10. A system for performing an interventional medical procedure, comprising:
    a treatment device including a distal end with a treatment portion;
    a localization system configured to provide a location of the treatment portion; and
    a processor configured to define, based on and relative to the location of the treatment portion as a respective location of the treatment portion changes during the procedure, a treatment path and an operational region along the treatment path;
    wherein the processor is further configured to provide a response whenever the location of the treatment portion, or a velocity or an acceleration of the treatment portion, violates a system parameter.

11. The system of claim 10, wherein the system parameter is configured to require that the location of the treatment portion remains within the operational region.

12. The system of claim 10, wherein the processor is further configured to define an acceptable velocity range for the velocity of the treatment portion along at least a portion of the treatment path, and wherein the system parameter is configured to require that the velocity of the treatment portion remains within the acceptable velocity range.

13. The system of claim 10, wherein the processor is further configured to define an acceptable acceleration range for the acceleration of the treatment portion along at least a portion of the treatment path, and wherein the system parameter is configured to require that the acceleration of the treatment portion remains within the acceptable acceleration range.

14. A method for preventing collateral damage in connection with an interventional medical procedure performed in a treatment environment with a treatment device comprising a distal end having a treatment portion, comprising:
    a. obtaining a location data point indicative of a location of the treatment portion;
    b. defining a boundary about the treatment portion based on and relative to the location data point as a respective location of the location data point changes during the procedure and defining an operational region within the boundary;
    c. determining whether the treatment portion is outside of the operational region;
    d. providing a response whenever the treatment portion is outside of the operational region;
    e. updating the boundary relative to the location data point;
    f. updating the operational region;
    g. updating the location data point; and
    h. repeating steps (c)-(g) during the interventional medical procedure.

15. The method of claim 14, wherein the providing step further comprises rendering the treatment portion inoperable whenever if a portion of the treatment portion is outside of the operational region.

16. A method for preventing collateral damage while using a treatment device in connection with an interventional medical procedure in a treatment environment, comprising:
- obtaining a location data point indicative of a location of a treatment portion of the treatment device;
- defining a treatment path based on and relative to the location data point as a respective location of the location data point changes during the interventional procedure and providing an operational region along the treatment path;
- determining whether a position or a movement of the treatment portion violates a system parameter; and
- providing a response if the position or the movement of the treatment portion violates the system parameter.

17. The method of claim 16, wherein the system parameter requires that the position of the treatment portion remains within the operational region.

18. The method of claim 16, wherein the defining step further comprises defining an acceptable velocity range for the movement of the treatment portion along at least a portion of the treatment path, and wherein the system parameter is configured to require that a velocity of the treatment portion remains within the the acceptable velocity range.

19. The method of claim 16, wherein the response includes rendering the treatment portion inoperable.

20. The method of claim 16, wherein the defining step further comprises defining an acceptable acceleration range for the movement of the treatment portion along at least a portion of the treatment path, and wherein the system parameter is configured to require that an acceleration of the treatment portion remains within the acceptable acceleration range.

* * * * *